(12) United States Patent
Mano

(10) Patent No.: US 7,943,909 B2
(45) Date of Patent: May 17, 2011

(54) FLUORESCENCE DETECTING APPARATUS AND FLUORESCENCE OBSERVATION SYSTEM

(75) Inventor: Shigeyuki Mano, Yokohama (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 12/482,608

(22) Filed: Jun. 11, 2009

(65) Prior Publication Data
US 2009/0250628 A1    Oct. 8, 2009

Related U.S. Application Data

(63) Continuation of application No. PCT/JP2007/001342, filed on Dec. 4, 2007.

(30) Foreign Application Priority Data

Dec. 13, 2006    (JP) .................................. 2006-335997

(51) Int. Cl.
*G01J 1/58* (2006.01)
*G01J 3/50* (2006.01)
*G02B 21/00* (2006.01)

(52) U.S. Cl. ...................... 250/458.1; 250/226; 359/368

(58) Field of Classification Search ............. 250/370.09, 250/458.1, 201.3; 359/368, 381, 388
See application file for complete search history.

(56) References Cited

U.S. PATENT DOCUMENTS

| 4,791,310 A * | 12/1988 | Honig et al. ............... 250/458.1 |
| 6,337,767 B1 * | 1/2002 | Takeuchi ...................... 359/388 |
| 7,417,211 B2 * | 8/2008 | Nakata et al. ............. 250/201.3 |
| 2006/0086887 A1 | 4/2006 | Nakata et al. |

FOREIGN PATENT DOCUMENTS

| JP | 07-281096 A | 10/1995 |
| JP | 2003-295064 A | 10/2003 |
| JP | 2004-13128 A | 1/2004 |
| JP | 2005-331889 A | 12/2005 |
| JP | 2006-119347 A | 5/2006 |
| JP | 2006-220954 A | 8/2006 |

* cited by examiner

*Primary Examiner* — David P Porta
*Assistant Examiner* — Faye Boosalis
(74) *Attorney, Agent, or Firm* — Miles & Stockbridge P.C.

(57) ABSTRACT

A fluorescence detecting apparatus includes a light detecting device disposed in a light path of fluorescence generated in an illuminated area of a specimen and a barrier filter disposed in the light path toward the light detecting device to exhibit transparency for each of a plurality of fluorescences having separated wavelength bands.

20 Claims, 8 Drawing Sheets

FLUORESCENCE DETECTING APPARATUS AND FLUORESCENCE OBSERVATION SYSTEM

CROSS REFERENCE TO THE RELATED APPLICATIONS

This application is a continuation application of International Application PCT/JP2007/001342, filed Dec. 4, 2007, designating the U.S., and claims the benefit of priority from Japanese Patent Application No. 2006-335997, filed on Dec. 13, 2006, the entire contents of which are incorporate herein by reference.

BACKGROUND

1. Field

The present invention relates to a fluorescence detecting apparatus applied to a fluorescence observation system such as a confocal laser fluorescence microscope system, and a fluorescence detecting system thereof.

2. Description of the Related Art

Generally, a photomultiplier (hereinafter referred to as "PMT") is used for a fluorescence detecting unit of a confocal laser fluorescence microscope. A barrier filter which transmits only the fluorescence of a particular wavelength band is disposed at the incident side of the PMT. Many fluorescence detecting units have a plurality of sets of PMTs and barrier filters mounted thereon in order to provide a plurality of wavelength bands (detecting channels) to be detected (see Patent Document 1: Japanese Unexamined Patent Application Publication No. 2006-220954, etc.). The number of sets of PMTs and barrier filters may be simply increased when providing additional detecting channels.

However, increasing the number of PMTs substantially increases the cost of the fluorescence detecting unit. Therefore, a method is conceivable in which a turret equipped with a plurality of barrier filters is used to switch the wavelength band of the fluorescence that can enter a single PMT (see Patent Document 2: Japanese Unexamined Patent Application Publication No. 2003-295064, etc.). By making the detecting channel of the PMT switchable in this manner, it becomes possible to increase the number of detecting channels while suppressing the number of PMTs.

However, acquiring a plurality of fluorescence images while switching the detecting channels of the PMT causes a time lag in the acquisition timing of individual fluorescence images.

Therefore, it is a proposition of the present invention to provide a fluorescence detecting apparatus which can easily speed up switching of detecting channels. In addition, it is also a proposition of the present invention to provide a fluorescence observation system which can acquire, at a low cost and as fast as possible, a plurality of fluorescence images having different wavelength bands.

SUMMARY

A fluorescence detecting apparatus of the present invention includes a light detecting device disposed in a light path of fluorescence generated in an illuminated area of a specimen, and a barrier filter disposed in the light path to exhibit transparency for at least two fluorescences among a plurality of fluorescences having different wavelength bands generated in the illuminated area of the specimen to be detected.

DETAILED DESCRIPTION OF THE EMBODIMENTS

Hereinafter, a confocal laser fluorescence microscope system to which the present invention is applied will be described.

First, a configuration of the present system will be described.

Figure 1:
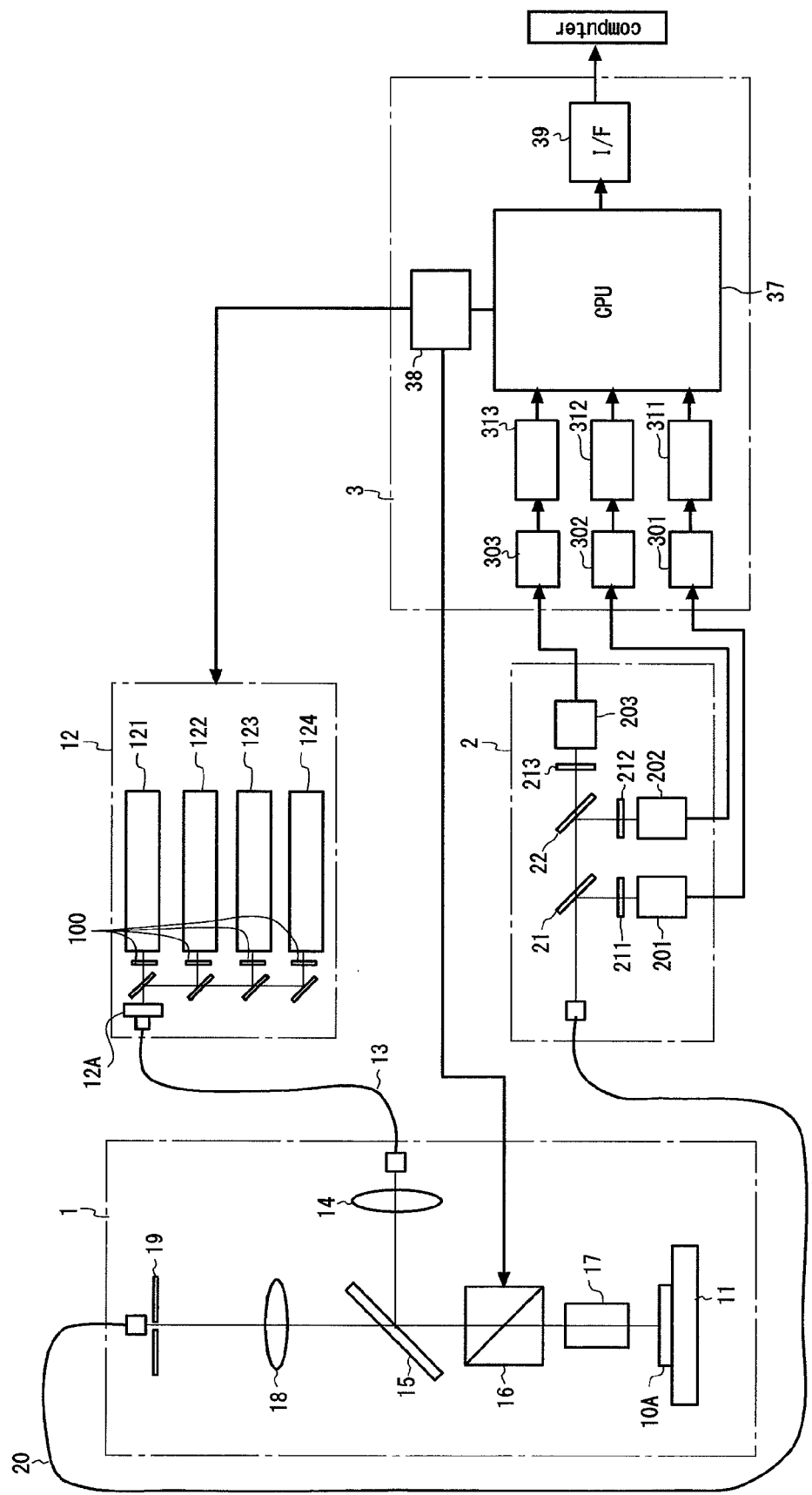
FIG. 1 is a configuration diagram of a confocal laser fluorescence microscope system.

FIG. 1 is a configuration diagram of a confocal laser fluorescence microscope system. As shown in FIG. 1, the present system includes a main body of microscope 1; a laser unit 12 connected to the main body of microscope 1 by an optical fiber 13; and a fluorescence detecting unit 2 connected to the main body of microscope 1 by an optical fiber 20. In addition, the present system includes a control unit 3 electrically connected to each of the main body of microscope 1, laser unit 12 and fluorescence detecting unit 2; and a computer (not shown) connected to the control unit 3 by a communication cable.

The laser unit 12 includes a first laser source 121, a second laser source 122, a third laser source 123, and a fourth laser source 124, which emit laser beams of mutually different wavelengths, respectively. The laser unit 12 includes a tunable filter 12A such as an AOTF and a shutter 100. The laser unit 12 can change the laser source being used, or perform on/off control of laser beams emitted from the laser unit 12, by combining the operation of the tunable filter 12A and the shutter 100.

The main body of microscope 1 includes a collimating lens 14, a dichroic mirror 15, a scanner 16, an objective lens 17, an imaging lens 18, a confocal diaphragm 19, and a stage 11. A specimen 10A is supported by the stage 11. The specimen 10A is a multistained specimen, in which a plurality of types of fluorescent materials having different excitation wavelengths coexists. Here, it is assumed that there are four types as the plurality of types of fluorescent materials: a first fluorescent material, a second fluorescent material, a third fluorescent material, and a fourth fluorescent material. The emission wavelength of the above-mentioned first laser source 121 is identical to the excitation wavelength of the first fluorescent material, the emission wavelength of the second laser source 122 is identical to excitation wavelength of the second fluorescent material, the emission wavelength of the third laser source 123 is identical to the excitation wavelength of the third fluorescent material, and the emission wavelength of the fourth laser source 124 is identical to the excitation wavelength of the fourth fluorescent material. Examples of these emission wavelengths will be described below.

The fluorescence detecting unit 2 includes a first dichroic mirror 21, a second dichroic mirror 22, a first barrier filter 211, a second barrier filter 212, a third barrier filter 213, a first PMT 201, a second PMT 202, and a third PMT 203. The first PMT 201, the second PMT 202, and the third PMT 203 are PMTs having identical characteristics, with their detection wavelength band being in the visible-light wavelength band (e.g., 400 nm to 750 nm). Note that the number of PMTs equipped in the fluorescence detecting unit 2 (three, in this case) is less than that of laser sources equipped in the laser unit 12 (four, in this case).

The control unit 3 includes a CPU 37, a control circuit 38, a first A/D converter 301, a second A/D converter 302, a third A/D converter 303, a first frame memory 311, a second frame memory 312, a third frame memory 313, and an interface circuit 39.

The laser beam emitted from the laser unit 12 is guided to the main body of microscope 1 via the optical fiber 13. The laser beam is focused on a single point on the specimen 10A via the collimating lens 14, the dichroic mirror 15, the scanner 16, and the objective lens 17 in sequence, and excites the fluorescent material existing at the focal point. For example, if the first laser source 121 is the only laser source for use by the laser unit 12, only the first fluorescent material is excited and only the first fluorescent material emits the fluorescence. In addition, if the second laser source 122 is the only laser source for use by the laser unit 12, only the second fluorescent material is excited and only the second fluorescent material emits the fluorescence. In addition, if the third laser source 123 is the only laser source for use by the laser unit 12, only the third fluorescent material is excited and only the third fluorescent material emits the fluorescence. In addition, if the fourth laser source 124 is the only laser source being used, only the fourth fluorescent material is excited and only the fourth fluorescent material emits the fluorescence. In the following, fluorescence emitted by the first fluorescent material, the fluorescence emitted by the second fluorescent material, the fluorescence emitted by the third fluorescent material, and the fluorescence emitted by the fourth fluorescent material are referred to as "the first fluorescence", "the second fluorescence", "the third fluorescence", and "the fourth fluorescence", respectively.

The fluorescence generated at the focal point (at least one of the first fluorescence to the fourth fluorescence) is focused near the opening of the confocal diaphragm 19 via the objective lens 17, the scanner 16, the dichroic mirror 15, and the imaging lens 18 in sequence. Among the above, the fluorescence which passed through the opening of the confocal diaphragm 19 is guided to the fluorescence detecting unit 2 via the optical fiber 20. Here, the focal point of the laser beam moves over the specimen 10A when the scanner 16 is driven. Additionally, in the main body of microscope, behaviors of the first fluorescence to the fourth fluorescence generated at the focal point are mutually identical. However, the first fluorescence to the fourth fluorescence behave in mutually different manners in the fluorescence detecting unit 2.

The first fluorescence which entered the fluorescence detecting unit 2 is reflected by the first dichroic mirror 21, transmitted through the first barrier filter 211, and proceeds toward the first PMT 201. The second fluorescence which entered the fluorescence detecting unit 2 is transmitted through the first dichroic mirror 21, reflected by the second dichroic mirror 22, transmitted through the second barrier filter 212, and proceeds toward the second PMT 202. The third fluorescence which entered the fluorescence detecting unit 2 is transmitted through the first dichroic mirror 21 and the second dichroic mirror 22 in sequence, transmitted through the third barrier filter 213, and proceeds toward the third PMT 203. The fourth fluorescence which entered the fluorescence detecting unit 2 is reflected by the first dichroic mirror 21, transmitted through the first barrier filter 211, and proceeds toward the first PMT 201.

In other words, the first dichroic mirror 21 exhibits reflectivity for the light in the wavelength band of the first fluorescence and the fourth fluorescence, and exhibits transparency for the light in the wavelength band of the second fluorescence and the third fluorescence. In addition, the first barrier filter 211 exhibits transparency for the light in the wavelength band of the first fluorescence and the fourth fluorescence, and exhibits absorptivity for light having other wavelength bands. As will be described in detail below, since the wavelength band of the first fluorescence and the wavelength band of the fourth fluorescence are separated from each other, a dual-path barrier filter which transmits light having a plurality of wavelength bands separated from each other is used for the first barrier filter 211.

The first PMT 201, the second PMT 202, and the third PMT 203 each generates a signal indicating the intensity of the incident light. The signal generated by the first PMT 201, the signal generated by the second PMT 202, and the signal generated by the third PMT 203 are input to the control unit 3.

The signal generated by the first PMT 201 is accumulated in the first frame memory 311 via the first A/D converter 301, the signal generated by the second PMT 202 is accumulated in the second frame memory 312 via the second A/D converter 302, and the signal generated by the third PMT 203 is accumulated in the third frame memory 313 via the third A/D converter 303.

In other words, a signal path of "the first PMT 201→the first A/D converter 301→the first frame memory 311" is used for both the signal of the first fluorescence and the signal of the fourth fluorescence. In addition, a signal path of "the second PMT 202→the second A/D converter 302→the second frame memory 312" is a signal path dedicated to the signal of the second fluorescence, and a signal path of "the third PMT 203→the third A/D converter 303→the third frame memory 313" is a signal path dedicated to the signal of the third fluorescence.

The control circuit 38 of the control unit 3 synchronously controls the scanner 16 and the laser unit 12, and scans the observation area on the specimen 10A at the focal point of the laser beam. During the scanning period of a single frame, a signal (fluorescence image signal) for a single frame is accumulated in at least one of the first frame memory 311, the second frame memory 312, and the third frame memory 313. The CPU 37 reads the fluorescence image signal and transmits it to the computer via the interface circuit 39. The above-mentioned operation procedure of the control unit 3 will be referred to as "image acquisition sequence" in the following.

Upon execution of the image acquisition sequence, the first fluorescence is generated and the fourth fluorescence is not generated at the focal point, if the control circuit 38 sets only the former of the first laser source 121 and the fourth laser source 124 as the laser source for use by the laser unit 12. In this occasion, the detecting channel of the first PMT 201 is accordingly set as the wavelength band of the first fluorescence, and a fluorescence image signal of the first fluorescence is accumulated in the first frame memory 311.

If, on the other hand, the control circuit 38 sets only the latter of the first laser source 121 and the fourth laser source 124 as the laser source for use by the laser unit 12, the first fluorescence is not generated and the fourth fluorescence is generated at the focal point. In this occasion, the detecting channel of the first PMT 201 is accordingly set as the wavelength band of the fourth fluorescence, and a fluorescence image signal of the fourth fluorescence is accumulated in the first frame memory 311.

Therefore, with the present system, the detecting channel of the first PMT 201 can be switched between the wavelength band of the first fluorescence and the wavelength band of the fourth fluorescence by simply switching the laser source for use by the laser unit 12 between the first laser source 121 and the fourth laser source 124 by the control circuit 38. The switching can be performed very fast, since a tunable filter 12A is used in the laser unit 12 as mentioned above.

Next, examples of characteristic of respective parts of the present system will be described.

emission wavelength of the first laser source 121 (=excitation wavelength of the first fluorescent material): 408 nm, emission wavelength of the second laser source 122 (=excitation wavelength of the second fluorescent material): 488 nm, emission wavelength of the third laser source 123 (=excitation wavelength of the third fluorescent material): 543 nm, emission wavelength of the fourth laser source 124 (=excitation wavelength of the fourth fluorescent material): 633 nm, stokes shift of the first fluorescent material: 25 nm,
stokes shift of the second fluorescent material: 25 nm,
stokes shift of the third fluorescent material: 25 nm,
stokes shift of the fourth fluorescent material: 25 nm, wavelength width of the fluorescence of the first fluorescent material (the first fluorescence): 30 nm (±15 nm)

wavelength width of the fluorescence of the second fluorescent material (the second fluorescence): 30 nm (±15 nm)

wavelength width of the fluorescence of the third fluorescent material (the third fluorescence): 30 nm (±15 nm)

wavelength width of the fluorescence of the fourth fluorescent material (the fourth fluorescence): 30 nm (±15 nm)

reflection wavelength band of the first dichroic mirror 21: under 449 nm, over 643 nm (449 nm to 643 nm is transmission wavelength band)

transmission wavelength band of the first barrier filter 211: 418 nm to 448 nm, 643 nm to 673 nm (under 418 nm, 448 nm to 643 nm, over 673 nm are absorption wavelength bands)

reflection wavelength band of the second dichroic mirror 22: under 529 nm (over 529 nm is transmission wavelength band)

transmission wavelength band of the second barrier filter 212: 498 nm to 528 nm (under 498 nm, over 528 nm are absorption wavelength bands)

transmission wavelength band of the third barrier filter 213: over 553 nm (under 553 nm is absorption wavelength band)

Figure 2A:
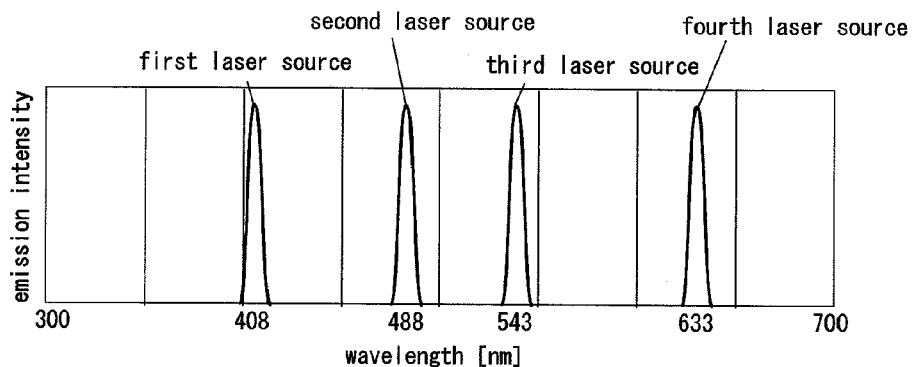
FIG. 2(A) illustrates emission wavelength characteristic of each laser source.

Drawn on the same graph, emission wavelength characteristic of respective laser sources in the above-mentioned embodiment are shown as in FIG. 2(A).

Figure 2B:
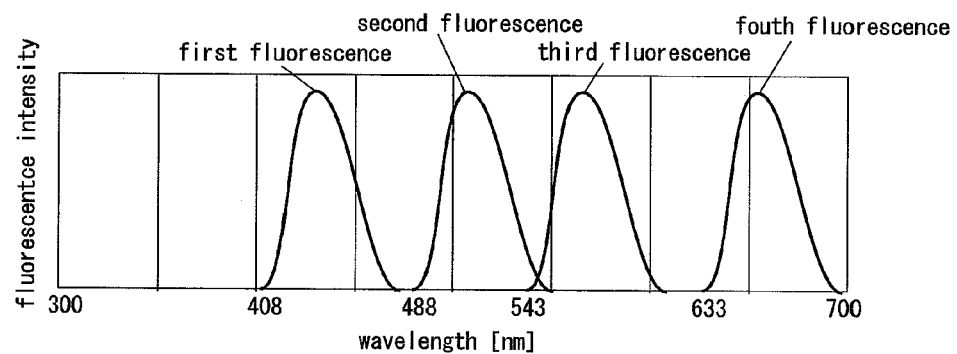
FIG. 2(B) illustrates fluorescence wavelength characteristic of each fluorescent material.

Additionally, drawn on the same graph, fluorescence wavelength characteristic of respective fluorescent materials are shown as in FIG. 2(B).

Figure 2C:
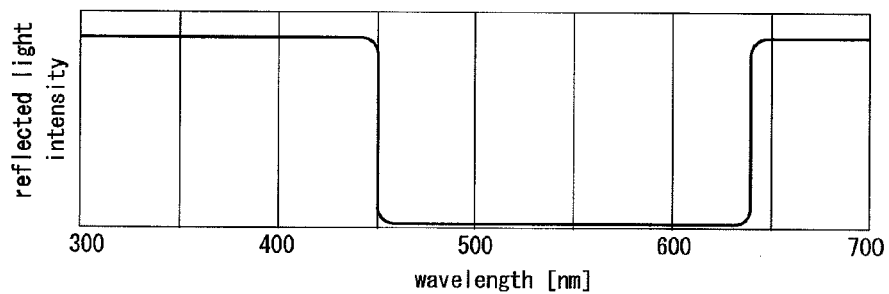
FIG. 2(C) illustrates reflection wavelength characteristic of a first dichroic mirror.
Figure 2D:
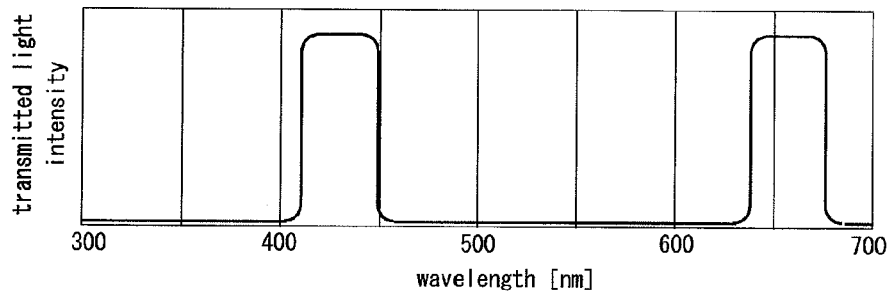
FIG. 2(D) illustrates reflection wavelength characteristic of a first barrier filter 211.

Additionally, drawn on a graph, reflection wavelength characteristic of the first dichroic mirror 21 are shown as in FIG. 2(C) and transmission wavelength characteristic of the first barrier filter 211 are shown as in FIG. 2(D).

Therefore, it is obvious that the detecting channel of the first PMT 201 is switched between the wavelength band of the first fluorescence and the wavelength band of the fourth fluorescence when the laser source being used is switched between the first laser source 121 and the fourth laser source 124.

Note that, in this example, since the detecting channels before and after the switching are sufficiently separated, a phenomenon that the fluorescence which has been generated immediately before the switching provides noise to the fluorescence image signal immediately after the switching (crosstalk) can be suppressed.

Figure 3A:
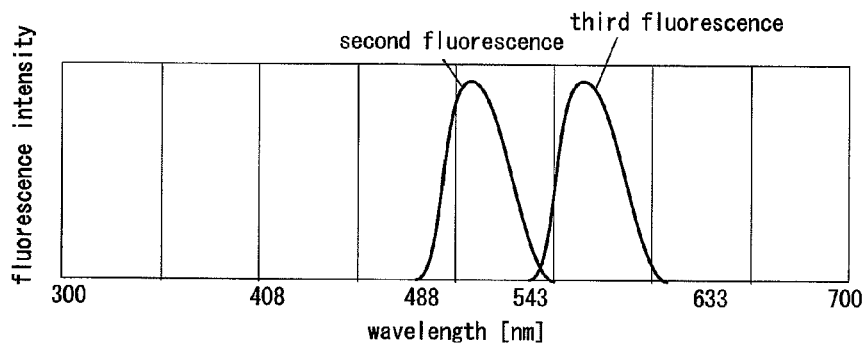
FIG. 3(A) illustrates fluorescence wavelength characteristic of fluorescence (a second fluorescence and a third fluorescence) which can reach a second dichroic mirror 22.
Figure 3B:
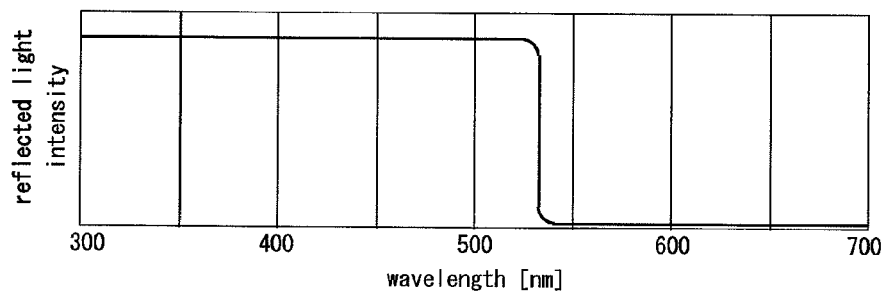
FIG. 3(B) illustrates reflection wavelength characteristic of the second dichroic mirror 22.
Figure 3C:
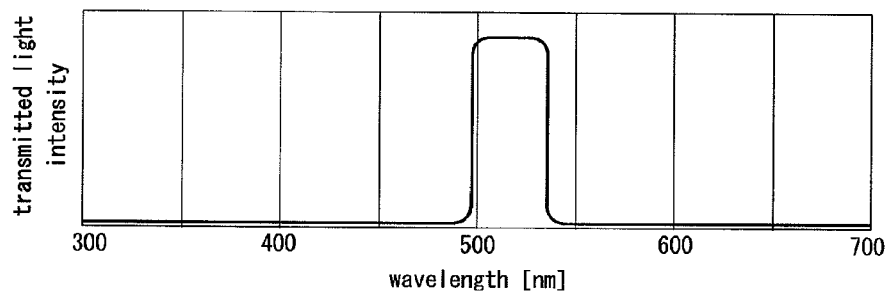
FIG. 3(C) illustrates transmission wavelength characteristic of a second barrier filter 212.
Figure 3D:
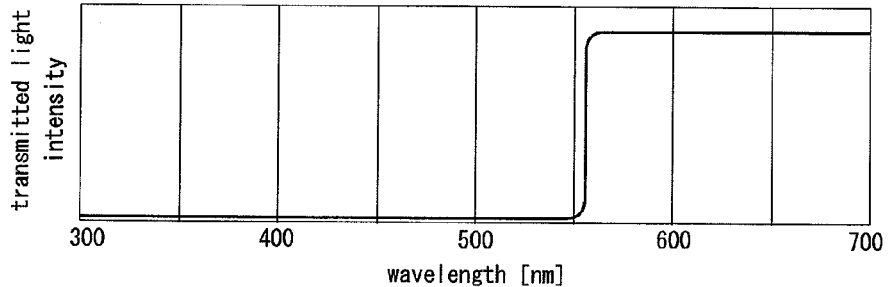
FIG. 3(D) illustrates transmission wavelength characteristic of a third barrier filter 213.

Additionally, by drawing on a graph, reflection wavelength characteristic of the second dichroic mirror 22 in the above-mentioned example are shown as in FIG. 3(B), and transmission wavelength characteristic of the second barrier filter 212 are shown as in FIG. 3(C). Here, fluorescence which can reach the second dichroic mirror 22 (the second fluorescence and the third fluorescence) is shown in FIG. 3(A). Therefore, it is obvious that the detecting channel of the second PMT 202 generally coincides with the wavelength band of the second fluorescence.

Additionally, by drawing on a graph, transmission wavelength characteristic of the third barrier filter 213 in the above-mentioned embodiment is shown as in FIG. 3 (D). Therefore, it is obvious that the detecting channel of the third PMT 203 generally coincides with the wavelength band of the third fluorescence.

Next, the computer of the present system will be briefly described.

Figure 4:
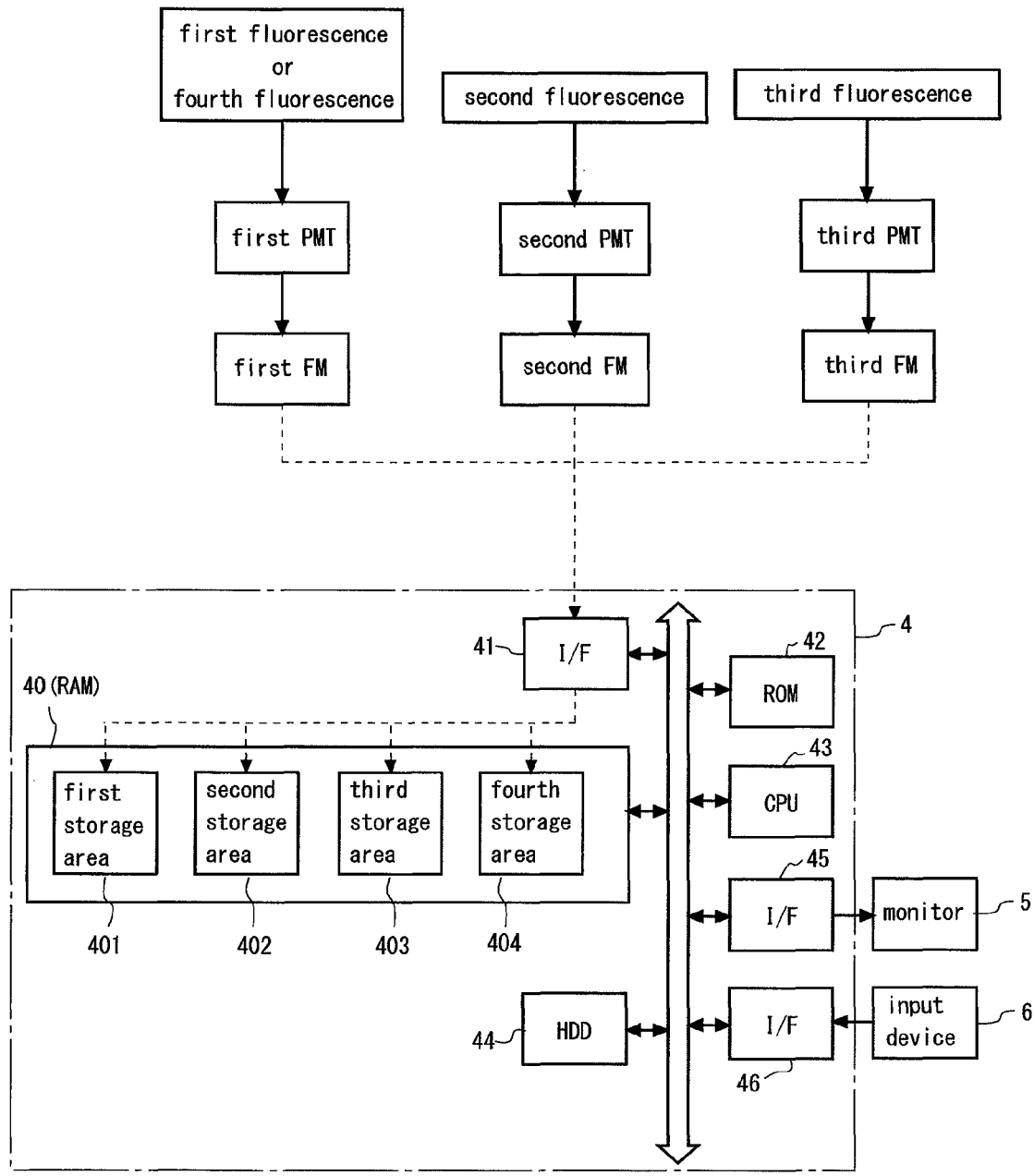
FIG. 4 is a configuration diagram of a computer.

FIG. 4 is a configuration diagram of the computer. A computer 4 includes a RAM 40, an interface circuit 41, a ROM 42, a CPU 43, a hard disk drive 44, an interface circuit 45, and an interface circuit 46. The computer 4 is coupled to a control unit 3 via the interface circuit 41, and coupled to a monitor 5 and an input device 6 via the interface circuit 45 and interface circuit 46.

A program of application software which causes the computer 4 to function as an information processing apparatus of the present system is stored in the hard disk drive 44. The program is read out to the RAM 40 as needed and executed by the CPU 43. Operation of the CPU 43 described below is assumed to follow the program.

The CPU 43, as well as displaying a GUI screen on the monitor 5 via the interface circuit 45, recognizes the action performed on the input device 6 via the interface circuit 46. In addition, the CPU 43 communicates with the CPU 37 of the control unit 3 via the interface circuit 41 to transmit and receive a variety of information.

In addition, the CPU 43 assigns four storage areas on the RAM 40, i.e., the first storage area 401, the second storage area 402, the third storage area 403 and the fourth storage area 404 as storage areas which store fluorescence image signals received from the control unit 3. Individual storage areas can store fluorescence image signals for a single frame.

Next, the entire operation flow of the present system will be described. Here, it is assumed that a "two excitation—two fluorescence image acquisition" by the first fluorescence reagent and the third fluorescence reagent, and a "two excitation—two fluorescence image acquisition" by the second fluorescence reagent and the fourth fluorescence reagent are performed successively.

Figure 5:
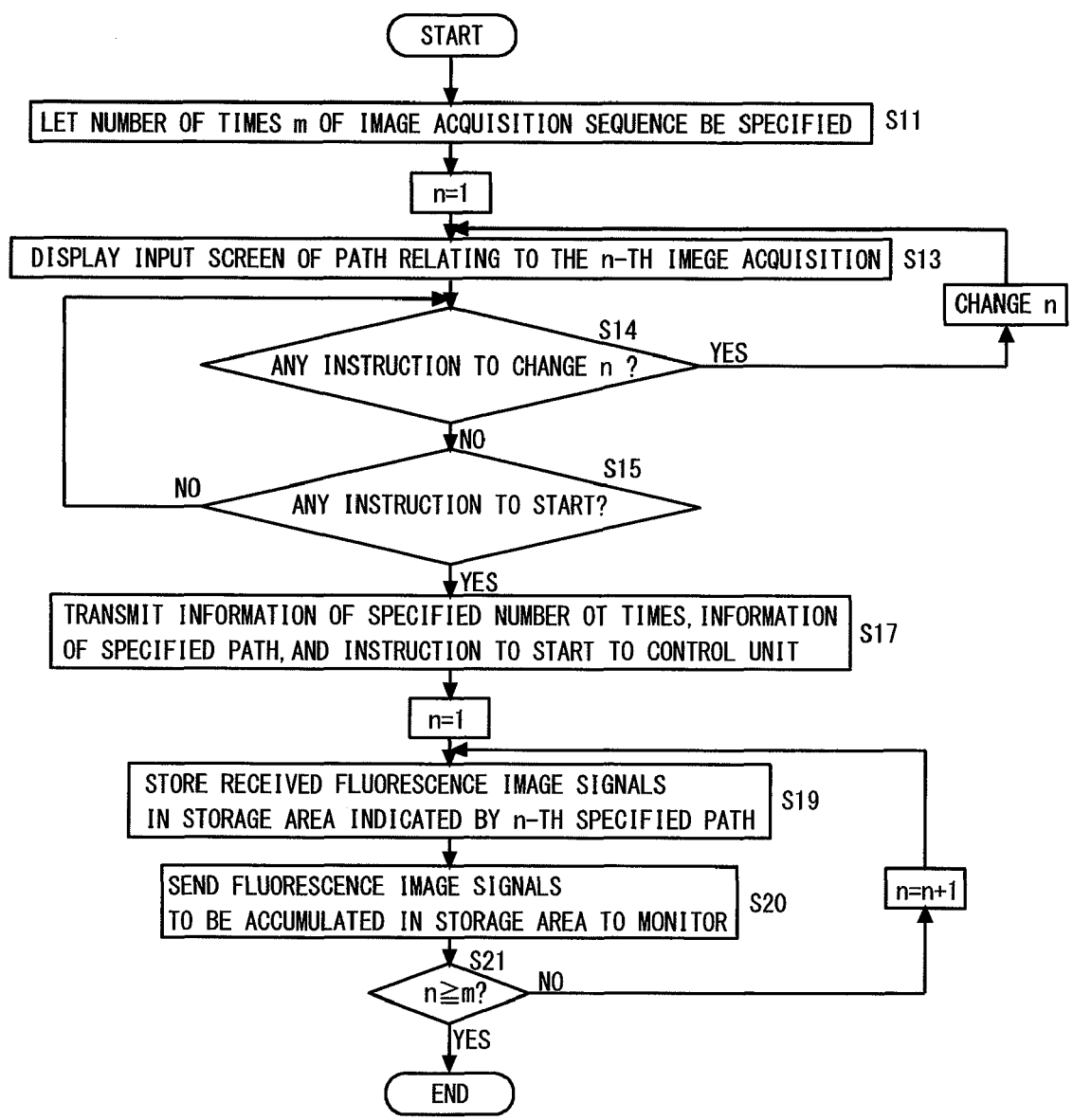
FIG. 5 is an operational flow chart of CPU 43 of the computer 4.

FIG. 5 is an operational flow chart of the CPU 43 of the computer 4.

First, the CPU 43 lets the user specify the number of times m of the image acquisition sequence (step S11). Here, "2" is specified as the number of times m. The number of times will be referred to as "specified number of times" in the following.

Subsequently, the CPU 43 displays an input screen 51 of a path relating to the first image acquisition sequence (FIG. 6) on the monitor 5 (step S13).

Figure 6:
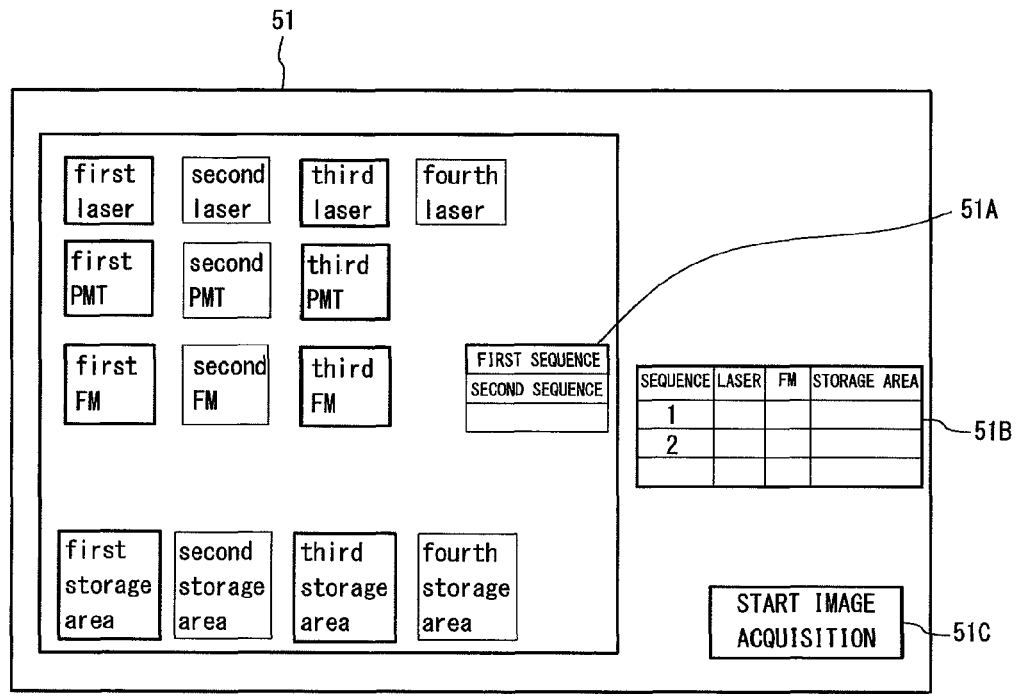
FIG. 6 is an input screen of a path with regard to first image acquisition sequence.

As shown in FIG. 6, each element of the present system, i.e., each of the marks of the first laser source to the fourth laser source, the first PMT to the third PMT, the first frame memory to the third frame memory, and the first storage area to the fourth storage area are arranged on the input screen 51. In addition, a setting list 51B indicating already input information, a switching button 51A, and a start button 51C are arranged on the input screen 51.

On the input screen 51, the user can specify, up to three routes, a path which should be set in the present system when executing the first image acquisition sequence.

Figure 7:
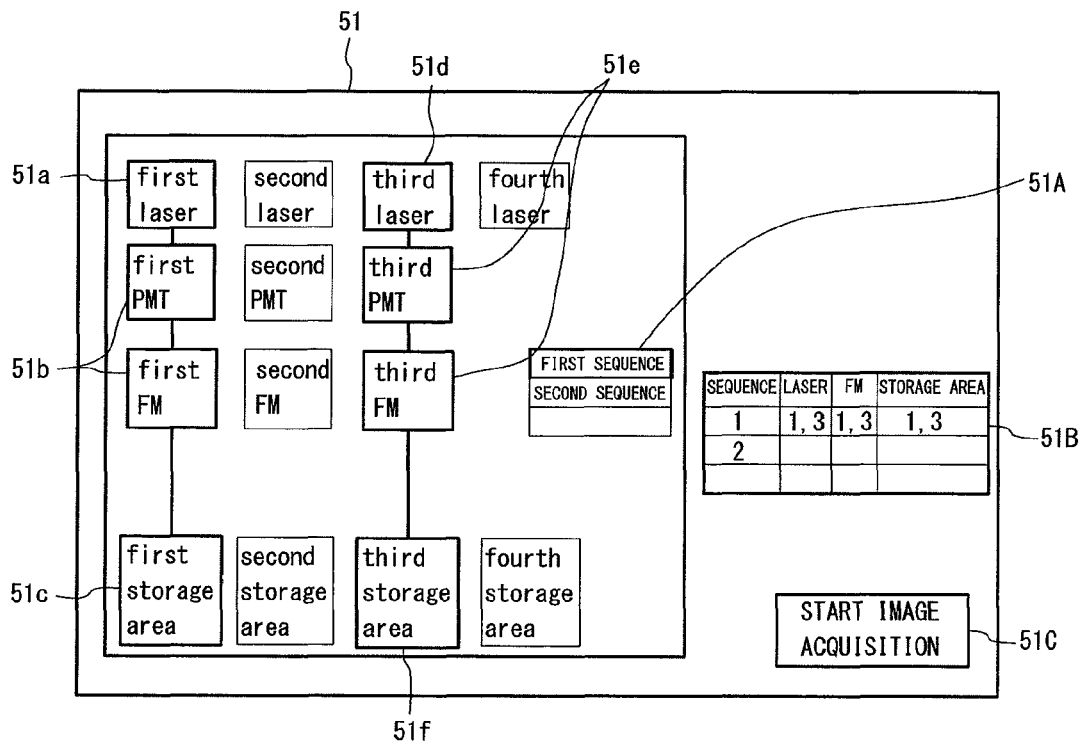
FIG. 7 is an input screen when a path is specified.

As shown in FIG. 7, the user successively selects, a mark 51a of the first laser source, a mark 51b of the first PMT or the first frame memory, and a mark 51c of the first storage area. In this occasion, a path of "the first laser source→the first PMT→the first frame memory→the first storage area" is drawn on the input screen 51 by an arrow line or the like. Information of this path is also reflected in the setting list 51B.

Additionally, on the same input screen 51, the user successively selects, a mark 51d of the third laser source, a mark 51e of the third PMT or the third frame memory, and a mark 51f of the third storage area. In this occasion, a path of "the third laser source→the third PMT→the third frame memory→the third storage area" is drawn on the input screen 51 by an arrow line or the like. Information of this path is also reflected in the setting list 51B.

Here, if one of the mark of the first PMT and the mark of the first frame memory is selected on the input screen 51 the other is also automatically selected, since the first PMT and the first frame memory are elements arranged on a common path.

In addition, if one of the mark of the second frame memory and the mark of the second PMT is selected on the input screen 51, the other is also automatically selected, since the second PMT and the second frame memory are elements arranged on a common path.

In addition, if one of the mark of the third PMT and the mark of the third frame memory is selected on the input screen 51, the other is also automatically selected, since the third PMT and the third frame memory are elements arranged on a common path.

The user views the input screen 51 and, if satisfied with the paths being displayed (here, path along two routes), operates the switching button 51A.

When the switching button 51A is operated (YES in step S14), the CPU 43 displays an input screen 52 of the path relating to the second image acquisition sequence (FIG. 8) on the monitor 5 (step S13) in place of the input screen 51 of the path relating to the first image acquisition sequence (FIG. 7).

Figure 8:
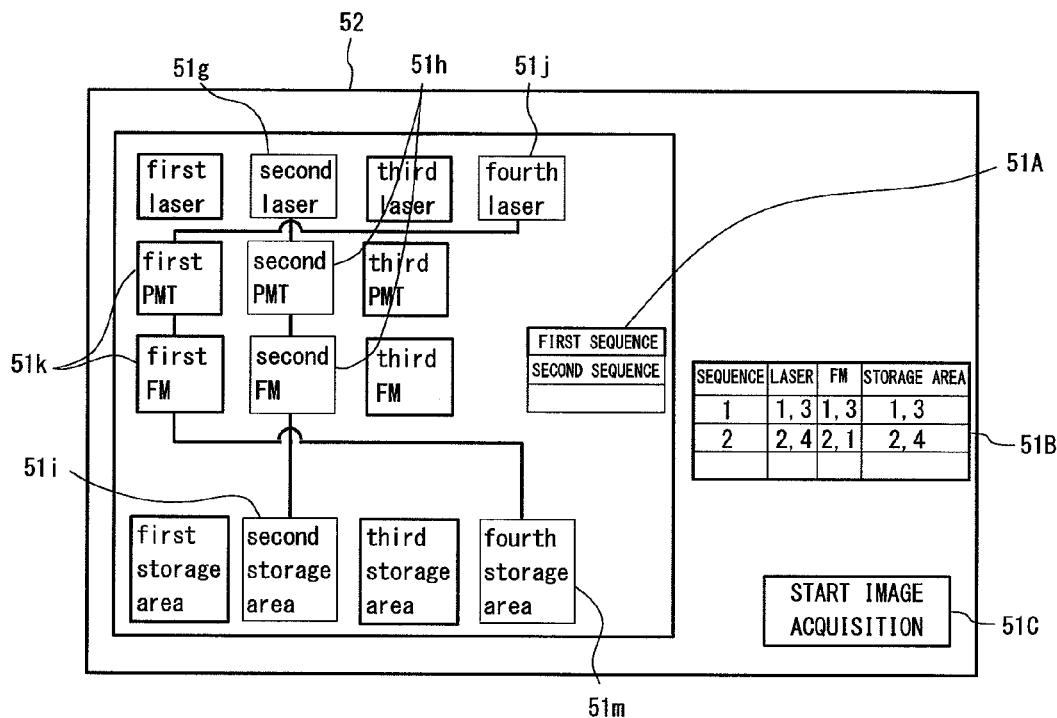
FIG. 8 is an input screen of a path with regard to second image acquisition sequence.

As shown in FIG. 8, the input screen 52 also has, as with the input screen 51 (FIG. 6), marks of respective elements of the present system, a setting list 51B, a switching button 51A, and a start button 51C arranged thereon. On the input screen 52, the user can specify, up to three routes, a path which should be set in the present system when executing the second image acquisition sequence.

As shown in FIG. 8, the user successively selects, a mark 51g of the second laser source, a mark 51h of the second PMT or the second frame memory, and a mark 51i of the second storage area. In this occasion, a path of "the second laser source→the second PMT→the second frame memory→the second storage area" is drawn on the input screen 52 by an arrow line or the like. Information of this path is also reflected in the setting list 51B.

Additionally, on the same input screen 52, the user successively selects a mark 51j of the fourth laser source, a mark 51k of the first PMT or the first frame memory, and a mark 51m of the fourth storage area. In this occasion, a path of "the fourth laser source→the first PMT→the first frame memory→the fourth storage area" is drawn on the input screen 52 by an arrow line or the like. Information of this path is also reflected in setting list 51B.

Here, it is assumed that, also on the input screen 52, if one of the mark of the first PMT and the mark of the first frame memory is selected the other is also automatically selected, if one of the mark of the second PMT and the mark of the second frame memory is selected the other is also automatically selected, and if one of the mark of the third PMT and the mark of the third frame memory is selected the other is also automatically selected.

The user views the input screen 52 and, if satisfied with the path being displayed (here, a path along two routes), operates the start button 51C.

In the following, the path specified by the user on the input screens 51 and 52 will be referred to as "the specified path", and particularly the path along the two routes specified on the input screen 51 (FIG. 7) will be referred to as "the first specified path" (the path which should be set in the first image sequence), and the path along the two routes specified on the input screen 52 (FIG. 8) will be referred to as "the second specified path" (the path which should be set in the second image sequence).

When the start button 51C is selected (YES in step S15), the CPU 43 recognizes the specified number of times and specified path reflected in the setting list 51B, and transmits the information of specified number of times, the information of specified path, and an instruction to start, to the control unit 3 (step S17).

Figure 9:
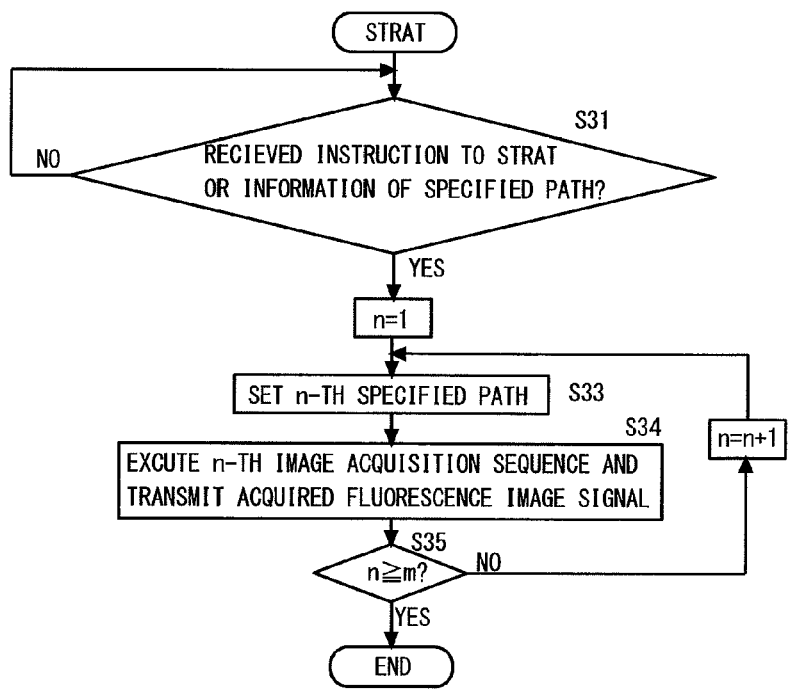
FIG. 9 is an operational flow chart of CPU 37 of a control unit 3.

FIG. 9 is an operational flow chart of the CPU 37 of the control unit 3.

Upon receiving the information of specified number of times, the information of specified path, and the instruction to start (YES in step S31), the CPU 37 sets (step S33) the path from the laser unit 12 to the control unit 3 as the first specified path (see FIG. 7), and executes the first image acquisition sequence under the setting (step S34).

Specifically, the CPU 37 instructs the control circuit 38 to set both the first laser source 121 and the third laser source 123 as the laser source for use by the laser unit 12, and subsequently starts the above-mentioned scanning, sequentially reads out two types of fluorescence image signals (a fluorescence image signal of the first fluorescence and a fluorescence image signal of the third fluorescence) to be respectively accumulated in the first frame memory 311 and the third frame memory 313 during the scanning period for a single frame, and transmits these fluorescence image signals to the computer 4 in a manner distinguished from each other.

Immediately after completion of the first image acquisition sequence, the CPU 37 sets the path from the laser unit 12 to the control unit 3 as the second specified path (step S33), and executes the second image acquisition sequence under the setting (step S34).

Specifically, the CPU 37 instructs the control circuit 38 to set both the second laser source 122 and the fourth laser source 124 as the laser source for use by the laser unit 12, and subsequently starts the above-mentioned scanning, sequentially reads out two types of fluorescence image signals (a fluorescence image signal of the fourth fluorescence and a fluorescence image signal of the second fluorescence) to be respectively accumulated in the first frame memory 311 and the second frame memory 312 during the scanning period for a single frame, and transmits these fluorescence image signals to the computer 4 in a manner distinguished from each other.

As shown in step S19 of FIG. 5, upon receiving a fluorescence image signal of the first fluorescence and a fluorescence image signal of the third fluorescence during execution of the first image acquisition sequence, the CPU 43 of the computer 4 stores these fluorescence image signals in the RAM 40 (step S19), following the first specified path (see FIG. 7). Specifically, the CPU 43 stores the fluorescence image signal of the first fluorescence in the first storage area 401, and stores the fluorescence image signal of the third fluorescence in the third storage area 403.

At the same time, the CPU 43 outputs, to the monitor 5, the fluorescence image signal of the first fluorescence to be stored in the first storage area 401 and the fluorescence image signal of the third fluorescence to be stored in the third storage area 403, respectively, via the interface circuit 45 (step S20).

Subsequently, upon receiving a fluorescence image signal of the fourth fluorescence and a fluorescence image signal of the second fluorescence during execution of the second image acquisition sequence, the CPU 43 of the computer 4 stores (step S19) these fluorescence image signals in the RAM 40, following the second specified path (see FIG. 8).

Specifically, the CPU 43 stores the fluorescence image signal of the fourth fluorescence in the fourth storage area 404, and stores the fluorescence image signal of the second fluorescence in the second storage area 402.

At the same time, the CPU 43 outputs, to the monitor 5, the fluorescence image signal of the fourth fluorescence to be stored in the fourth storage area 404 and the fluorescence image signal of the second fluorescence to be stored in the second storage area 402, respectively, via the interface circuit 45 (step S20).

Here, the fluorescence image signal of the first fluorescence, the fluorescence image signal of the second fluorescence, the fluorescence image signal of the third fluorescence, and the fluorescence image signal of the fourth fluorescence, which have been read out from mutually different storage areas are output to mutually different regions on the monitor 5.

As a result of the above, with the present system, the "two excitation—two fluorescence image acquisition" by the first fluorescence reagent and the third fluorescence reagent, and the "two excitation—two fluorescence image acquisition" by the second fluorescence reagent and the fourth fluorescence reagent are executed in succession, whereby a total of four types of fluorescence images are acquired.

Among these, between the former image acquisition and the latter image acquisition, the path of the present system is changed from the first specified path (see FIG. 7) to the second specified path (see FIG. 8). In this occasion, the detecting channel of the first PMT 201 is switched from the wavelength band of the first fluorescence to the wavelength band of the fourth fluorescence. However, since the switching of the detecting channel of the first PMT 201 is performed very fast as stated above, time lag between the former image acquisition and the latter image acquisition is suppressed to be very short.

Although it is assumed in the above description that the "two excitation—two fluorescence image acquisition" by the first fluorescence reagent and the third fluorescence reagent and the "two excitation—two fluorescence image acquisition" by the second fluorescence reagent and the fourth fluorescence reagent are performed successively, a variety of other implementation, for example, performing a "three excitation—three fluorescence image acquisition" by the first fluorescence reagent, the second fluorescence reagent and the third fluorescence reagent, and a "three excitation—three fluorescence image acquisition" by the second fluorescence reagent, the third fluorescence reagent and the fourth fluorescence reagent successively, may be employed by using the present system. Employing any of the implementations, time lag between the former image acquisition and the latter image acquisition can be suppressed to be very short.

In addition, although the present system lets the user select the entire route of the path which should be set in the image acquisition sequence, a part of the route of the path may be automatically selected by the computer 4.

For example, it may be arranged such that the user can simply select a mark of the first laser source on the input screens 51 and 52 to cause the path of "the first laser source→the first PMT→the first frame memory→the first storage area" to be automatically selected; the user can simply select a mark of the second laser source to cause the path of "the second laser source→the second PMT→the second frame memory→the second storage area" to be automatically selected; the user can simply select a mark of the third laser source to cause the path of "the third laser source→the third PMT→the third frame memory→the third storage area" to be automatically selected; and the user can simply select a mark of the fourth laser source to cause the path of "the fourth laser source→the fourth PMT→the fourth frame memory→the fourth storage area" to be automatically selected.

In addition, although the image acquisition method employed in the present system is a frame sequential acquisition method which acquires a plurality of fluorescence images per frame, a line sequential acquisition method which acquires a plurality of fluorescence images per line may be possible.

As has been stated above, since the switching of detecting channel of the first PMT 201 is performed very fast in the present system, a line sequential acquisition method can also be employed also in a case where a plurality of fluorescence images having different wavelength bands is acquired by the first PMT. However, in such a case, it is desirable to transform the present system as shown in FIG. 10.

Figure 10:
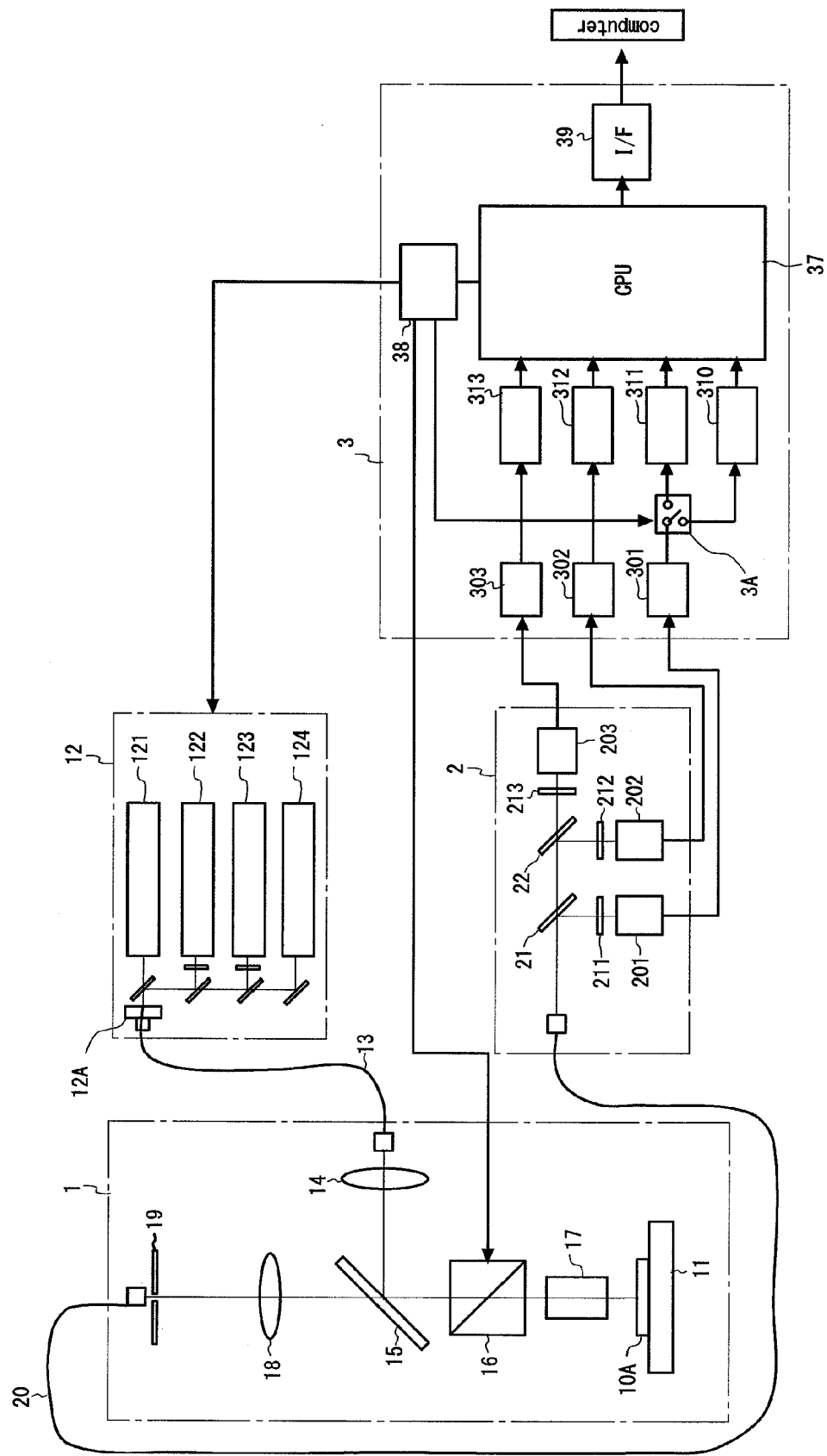
FIG. 10 is a configuration diagram of a variation of the present system.

In the system shown in FIG. 10, one frame memory is added to the control unit 3. In FIG. 10, a code 310 is provided to the additional frame memory. In addition, a switching device 3A is provided between the first A/D converter 301 and the first frame memory 311. The additional frame memory 310 is coupled to the switching device 3A.

The switching device 3A can switch a connection destination of the first A/D converter 301 between the first frame memory 311 and the additional frame memory 310 at a high speed.

When acquiring an image, the control circuit 38 of the system shown in FIG. 10 performs synchronous control of three components, i.e., the scanner 16, the laser unit 12, and the switching device 3A, and scans the same line in the observation area twice at the focal point. In addition, between the first scanning period and the second scanning period of the same line, the control circuit 38 switches the laser source for use by the laser unit 12 and switches the connection destination of the first A/D converter 301.

For example, it is assumed that, as the combination of the laser source for use by the laser unit 12 and the connection destination of the first A/D converter 301, a combination of the first laser source 121 and the first frame memory 311 is set during the first scanning period of the same line, whereas a combination of the fourth laser source 124 and the additional frame memory 310 is set during the second scanning period of the same line.

In this case, fluorescence image signals of the first fluorescence are accumulated in the first frame memory 311 and fluorescence image signals of the fourth fluorescence are accumulated in the additional frame memory 310, respectively, by the time scanning of the entire observation area is completed.

As thus described, by employing a line sequential acquisition method, it is possible to generally match the acquisition timing of fluorescence images of the first fluorescence using the first PMT 201 with the acquisition timing of fluorescence images of the fourth fluorescence using the first PMT 201.

The many features and advantages of the embodiments are apparent from the detailed specification and, thus, it is intended by the appended claims to cover all such features and advantages of the embodiments that fall within the true spirit and scope thereof. Further, since numerous modifications and changes will readily occur to those skilled in the art, it is not desired to limit the inventive embodiments to the exact construction and operation illustrated and described, and accordingly all suitable modifications and equivalents may be resorted to, falling within the scope thereof.

What is claimed is:

1. A fluorescence detecting apparatus comprising:
    a light detecting device disposed in a light path of fluorescence generated in an illuminated area of a specimen; and
    a barrier filter disposed in the light path to exhibit transparency for at least two fluorescences among a plurality of fluorescences having different wavelength bands generated in the illuminated area of the specimen to be detected,
    wherein the light detecting device and the barrier filter are arranged such that the two fluorescences transmitted through the barrier filter follow the same light path until detected by the light detecting device.

2. The fluorescence detecting apparatus according to claim 1, wherein
    the barrier filter is disposed immediately before a fluorescence incident side of the light detecting device.

3. The fluorescence detecting apparatus according to claim 1, wherein
    the barrier filter is disposed so as to be paired with the light detecting device.

4. The fluorescence detecting apparatus according to claim 1 further comprising:
    a dichroic mirror disposed at the fluorescence incident side of the barrier filter, the dichroic mirror reflecting fluorescences of at least two different wavelength bands among the plurality of fluorescences having different wavelength bands, and transmitting fluorescences of at least one wavelength band among the fluorescences of the remaining wavelength bands.

5. The fluorescence detecting apparatus according to claim 4, wherein
    the dichroic mirror includes at least a first dichroic mirror which reflects the fluorescences of at least two different wavelength bands among the fluorescences generated in the illuminated area and transmits the fluorescences of at least one wavelength band among the remaining fluorescences, and a second dichroic mirror which reflects the fluorescences of at least one wavelength band transmitted through the first dichroic mirror,
    the barrier filter includes at least a first barrier filter which transmits the fluorescences of at least two different wavelength bands reflected by the first dichroic mirror, and a second barrier filter which transmits the fluorescences of at least one wavelength band reflected by the second dichroic mirror, and
    the light detecting device includes at least a first light detecting device into which the fluorescences of at least two different wavelength bands transmitted through the first barrier filter are incident, and a second light detecting device into which the fluorescences of at least one wavelength band reflected by the second dichroic mirror are incident.

6. A fluorescence observation system comprising:
    a fluorescence detecting apparatus according to claim 1; and
    a control unit which sets a wavelength of illumination light incident into the illuminated area to be at least one of a plurality of excitation wavelengths required for generating any of the plurality of fluorescences, the control unit being configured to set a detecting channel of the light detecting device.

7. The fluorescence observation system according to claim 6, wherein
    the control unit acquires a plurality of fluorescence image signals of different wavelength bands from the light detecting device at mutually different timings, while switching the detecting channel.

8. The fluorescence observation system according to claim 7, wherein
    the control unit performs switching of the detecting channel on a per-frame basis.

9. The fluorescence observation system according to claim 7, wherein
    the fluorescence observation device includes a light scanning apparatus which scans the specimen in the illuminated area, and
    the control unit performs switching of the detecting channel on a per-line basis.

10. The fluorescence observation system according to claim 7 further comprising
    an information processing apparatus which takes in a plurality of fluorescence image signals acquired by the control unit, and stores the plurality of fluorescence image signals in mutually different memory spaces individually.

11. The fluorescence observation system according to claim 6 further comprising
    a monitor which displays at least a plurality of marks respectively corresponding to a plurality of light sources, a plurality of marks respectively corresponding to a plurality of light detecting devices, and a plurality of marks respectively corresponding to a plurality of storage units, wherein
    when marks are selected from respective items, namely the light sources, the light detecting devices, and the storage units, the control unit displays a path by drawing lines between the selected marks of respective items.

12. A fluorescence observation system comprising:
    a fluorescence detecting apparatus according to claim 1; and an A/D converter which processes signals obtained when the fluorescence of at least two different wavelength bands enter the light detecting device, as two mutually different signals, wherein the two different signals converted by the A/D converter are stored as different image signals in a single memory, respectively.

13. The fluorescence observation system according to claim 12, further comprising:

light sources which emit light of different wavelengths, respectively;

a tunable filter disposed in the light path of the lights from the light sources.

14. The fluorescence observation system according to claim 13, further comprising an optical system which collects the light from the light sources to form a single light path, wherein the tunable filter is disposed in the light path of the optical system.

15. The fluorescence observation system according to claim 13, wherein the light sources are at least two light sources which emit at least two lights of different wavelengths respectively.

16. The fluorescence observation system according to claim 12, wherein a plurality of marks can be selected from each of the same items, and when a plurality of marks is selected from each of the same items, a plurality of paths including each of the selected marks is displayed simultaneously.

17. A fluorescence detecting apparatus comprising:

a light detecting device disposed in a light path of fluorescence generated in an illuminated area of a specimen;

a barrier filter disposed in the light path to exhibit transparency for at least two fluorescences among a plurality of fluorescences having different wavelength bands, the barrier filter being disposed immediately before a fluorescence incident side of the light detecting device, and so as to be paired with the light detecting device;

a plurality of storage areas accumulating fluorescence image signals corresponding to the plurality of fluorescences having different wavelength bands which are transmitted through the barrier filter and are incident on the light detecting device; and a switching device switching the destination of the fluorescence image signals to corresponding storage areas so as to have fluorescence image signals of one wavelength band accumulating in one storage area and fluorescence image signals of a different wavelength band accumulating in another storage area.

18. A fluorescence observation system comprising the fluorescence detecting apparatus according to claim 17, wherein the fluorescence detecting apparatus includes at least two light sources which emit light of different wavelengths, respectively, an optical system which collects the light from the light sources to form a single light path, a tunable filter disposed in the single light path, a scanner which scans the light from the light sources on the specimen, and a control unit which synchronously controls the scanner, the light sources, and the switching device.

19. The fluorescence observation system according to claim 18, wherein the control unit scans a same line using the light of different wavelengths when scanning the specimen.

20. The fluorescence observation system according to claim 19, wherein the control unit switches the light source to be used for scanning between a first scanning period and a second scanning period when scanning of the same line is done using the light of different wavelengths.

* * * * *